United States Patent [19]

Reynolds

[11] 3,932,415

[45] Jan. 13, 1976

[54] PYRYLIUM DYES HAVING A FUSED RIGIDIZED NITROGEN-CONTAINING RING

[75] Inventor: George A. Reynolds, Rochester, N.Y.

[73] Assignee: Eastman Kodak Company, Rochester, N.Y.

[22] Filed: Aug. 20, 1973

[21] Appl. No.: 389,936

Related U.S. Application Data

[60] Division of Ser. No. 244,916, April 17, 1972, Pat. No. 3,822,270, which is a continuation-in-part of Ser. No. 170,349, Aug. 9, 1971, abandoned.

[52] U.S. Cl..... 260/286 R; 260/283 PF; 260/287 P; 260/289 CF; 331/94.5
[51] Int. Cl.². ....................................... C07D 215/58
[58] Field of Search............ 260/289, 287 R, 288 R, 260/286 PF

[56] References Cited

UNITED STATES PATENTS 3,822,270    7/1974    Reynolds.......................... 260/287 R

FOREIGN PATENTS OR APPLICATIONS 2,238,050    2/1973    Germany.......................... 260/287 R

*Primary Examiner*—Donald G. Daus
*Assistant Examiner*—David E. Wheeler
*Attorney, Agent, or Firm*—A. H. Rosenstein

[57] ABSTRACT

A class of pyrylium dyes, having at least one rigidized, nitrogen-containing heterocyclic ring fused thereto is described. The rigidized dyes are useful lasing components in lasing media.

4 Claims, No Drawings

PYRYLIUM DYES HAVING A FUSED RIGIDIZED NITROGEN-CONTAINING RING

This is a division of U.S. Ser. No. 244,916 filed Apr. 17, 1972 now U.S. Pat. No. 3,822,270.

U.S. Ser. No. 244,916 is a continuation-in-part application based on Ser. No. 170,349 filed Aug. 9, 1971 now abandoned.

This invention relates to a novel class of pyrylium dye having a fused, rigidized nitrogen-containing ring.

Compounds of the hereinafter described type are more rigid in configuration than the corresponding uncyclized amino-substituted dyes. Such uncyclized amino-substituted dyes have utility in dye laser applications; however, it is desirable to utilize dyes having a lower lasing threshold energy.

It is, therefore, an object of this invention to provide a class of novel compounds.

It is another object of this invention to provide new pyrylium compounds having a fused, rigidized nitrogen-containing ring.

Still a further object of this invention is to provide a class of novel lasing compounds which have a reduced lasing threshold energy.

These and other objects and advantages are accomplished by providing a class of (1) pyrylium salt compounds, having fused thereto at least at the [b] face, and preferably at each of the [b] and [e] faces, a rigidized, nitrogen-cotaining heterocyclic ring system having the structure:

I.
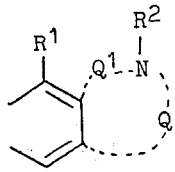

wherein one of Q and $Q^1$ represents the atoms necessary to form a saturated, divalent alkylene chain having 2 to 4 carbon atoms and which completes a fused, 5- to 7-membered heterocyclic ring rigidized by saturation of all atoms except those of the adjacent aromatic ring to which it is fused and the other of Q and $Q^1$ represents a chemical bond; and $R^1$ and $R^2$, when taken separately, each represent a hydrogen atom, an alkyl radical of 1 to about 10 carbon atoms, and when taken together, represent the carbon atoms necessary to form another alkylene chain as described for Q, said ring structure being fused to the pyrylium nucleus such that $R^1$ is only 2 carbon atoms removed from the oxygen atom of the pyrylium nucleus; and (2) the keto tautomers of said pyrylium compounds. The fused, rigidized ring is referred to herein as a saturated ring although it can be seen that the carbon atoms of the adjacent aromatic ring to which the rigidized ring is fused, and which form a part of the rigidized ring, are unsaturated.

More specifically, the preferred compounds of this invention conform to the structure:

II.
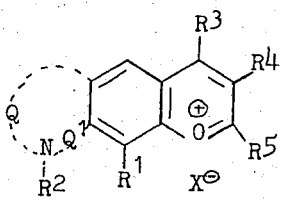

wherein one of Q and $Q^1$ represents a saturated, divalent alkylene chain having 2 to 4 carbon atoms and the other represents a chemical bond, $R^1$ and $R^2$ are as defined for Structure I; $R^3$ is a hydrogen atom, an alkyl group having 1 to about 10 carbon atoms including substituted alkyl, an aryl or substituted aryl group having 6 to 20 carbon atoms such as phenyl, carboxyphenyl, ethoxycarbonylphenyl, and the like, or when taken together with $R^4$, represents the atoms necessary to complete a fused 5- to 7-membered ring; $R^4$ is a hydrogen atom, and when taken together with $R^3$ represents the atoms necessary to complete a fused 5- or 7-membered ring, and when taken together with $R^5$, represents a substituted or unsubstituted fused ring or fused ring system, preferably a hydroxy-substituted benzo ring or a fused ring system as described by, and fused in the manner specified for, Structure I; $R^5$ is a hydrogen atom, a hydroxy group, or is taken together with $R^4$ to represent the fused ring or fused ring system specified above; and $X^-$ is an anion such as halide, perchlorate, fluoroborate, etc.

It is to be understood that the hydroxy compounds can tautomerize to the keto or enol forms depending on the pH of the solution in which they exist, or from which they are isolated. When isolated from hydroxylic organic solvents (see reaction below)

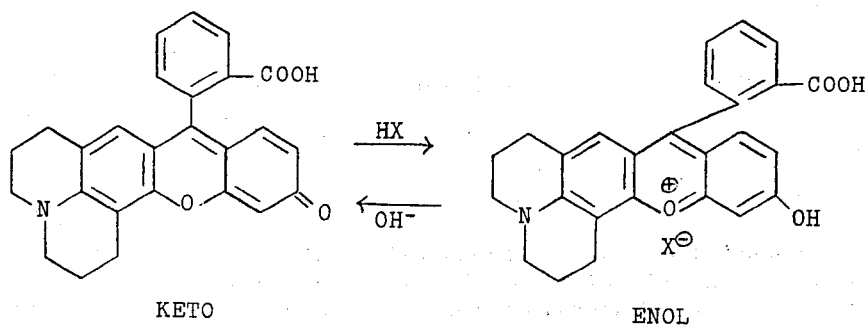

KETO                    ENOL such as ethanol, they generally assume the keto form since they are themselves weakly basic. The novel compounds of this invention thus include both the pyrylium salts described and the keto compounds derived therefrom simply by adjusting pH. The compounds can be isolated in either form.

Included compounds of this invention which can be in the keto form are represented by the formula:

III.

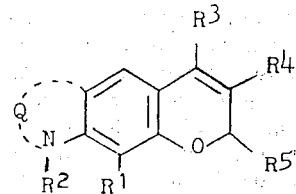

wherein Q, R¹ and R² are as described above; R³ represents a hydrogen atom, an alkyl group having 1 to about 10 carbon atoms and typically 1 to about 4 carbon atoms, an aryl radical including substituted aryl radicals such as phenyl, carboxyphenyl, naphthyl, ethoxycarbonyl phenyl and when taken together with R⁴ represents the carbon atoms necessary to complete a 5- or 6-membered fused ring; R⁴, represents a hydrogen atom, when taken together with R³ represents the carbon atoms necessary to complete a 5- or 6-membered fused ring and when taken together with R⁵, represents a fused oxobenzo moiety; and R⁵ alone represents an oxo moiety or when taken together with R⁴ represents the atoms necessary to complete a fused oxobenzo moiety.

In general, the compounds of the invention fall into two general categories, those having a single substituent as described by Structure I, i.e., monocompounds, and those containing two such substituents, i.e., bis-compounds. The bis-compounds are prepared by reacting an anhydride, preferably a phthalic anhydride, with an aminophenol in the presence of zinc chloride as described by H. S. Fierz-David Kunstlich Organische Farbstoffe, pages 275-6, Berlin (1926), using as the aminophenol an 8-hydroxyjulolidine as described in the Journal of the American Chemical Society, 86, 2533 (1964), or by reacting the 8-hydroxyjulolidine with an aldehyde and dehydrating with a strong acid, e.g., sulfuric acid.

The monocompounds are prepared by condensing 8-hydroxyjulolidine, as the aminophenol, with a β-keto ester, the latter providing compounds most easily isolated in the keto form, e.g., as coumarins which also operate well in lasing media in that form.

The following examples further illustrate the present invention.

EXAMPLE 1

Preparation of 8-Hydroxyjulolidine

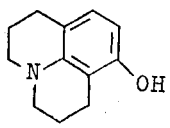

m-Anisidine (100 g) and 1 kg. of 1-bromo-3-chloropropane are heated in an oil bath at 150°C for 24 hours. Excess 1-bromo-3-chloropropane is removed by steam distillation. The solution is made basic with sodium hydroxide solution, decanted from some tar, and then extracted with methylene chloride. The aqueous phase is separated, neutralized by adding dry ice, and the precipitated solid collected, dried, and crystallized from ethanol.

Yield = 40 g. mp = 126°–128°C
Infrared and NMR spectra agree with the assigned structure.

EXAMPLE 2

Preparation of 9-(2-Carboxyphenyl)2,3,6,7,12,13,16,17-octahydro-1H,5H,11H,15H-diquinolizino[1,9-bc;1', 9'-hi]-xanthylium chloride

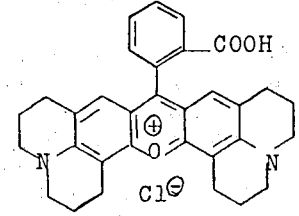

A mixture of 8.4 g (0.0445 mole) of the 8-hydroxyjulolidine prepared in Example 1, 6 g (0.0405 mole) of phthalic anhydride, and 3 g. of powdered zinc chloride is stirred and heated in an oil bath at 165°C for 5 hours. The melt is cooled and powdered, washed with water, filtered, triturated with sodium hydroxide solution, warmed to about 50°C, and diluted with water. The gum which separates is collected, washed with more sodium hydroxide solution and with water. The resulting dye base is then triturated with dilute hydrochloric acid and finally more concentrated hydrochloric acid is added. The dye is collected and dried.

Yield = 12 g.

A 3 g. sample is chromatographed on silica gel-cellulose by the ascending technique using chloroform and methanol (4:1), mp = 320°–325°C (dec).

Analysis calculated for $C_{32}H_{31}ClN_2O_3$: C, 72.9; H, 5.9. Found: C, 72.8; H, 5.9. A sample of the above chloride salt is converted to the perchlorate salt by dissolving in a small amount of hot methanol, and adding perchloric acid (70%). The mixture is diluted with water, and the solid collected and recrystallized from ethanol.

EXAMPLE 3

Preparation of 2,3,6,7,12,13,16,17-octahydro-1H,5H, 11H,15H-Diquinolizino[1,9-bc;1',9'-hi]xanthylium chloride

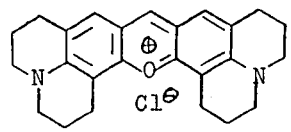

To a solution of 9.5 g. (0.05 mole) of 8-hydroxyjulolidine in ethanol is added 2 ml. of 40% formalin, after which the mixture is allowed to stand several days. The resultant yellow solid is collected and dried. The yield is 9 g. of bis(8-hydroxy-9-julolidyl)methane melting at 182°–183°C.

Analysis Calculated for $C_{25}H_{30}N_2O_2$: C,76.9; H, 7.7; N, 7.2. Found: C,77.0; H, 8.0; N, 7.0.

The bis(8-hydroxy-9-julolidyl)methane (5.8 g.) is gradually added with stirring to 20 ml. of concentrated sulfuric acid. The mixture is heated 3 hours on a steam bath, cooled and poured into about 100 g. of chopped ice. Concentrated sodium hydroxide is added until the mixture is just weakly acidic, 10 ml. of concentrated hydrochloric acid is added, and then a solution of 2 g.

of sodium nitrite in water is added dropwise with stirring. After standing overnight, the solid is collected, dried, and a sample chromatographed as in Example 2 on silica gel-cellulose by the ascending method using 1:1 methanol:chloroform. A un spectrum agrees with the assigned structure and the extinction coefficient ($1.2 \times 10^5$) of the long wave length band indicates a relatively high degree of purity.

EXAMPLE 4

Preparation of
1,2,3,4,5,6-Hexahydro-8-methylquinolazino [1,8a,8-gh]coumarin

A mixture of 5.7 g. (0.03 mole) of 8-hydroxyjulolidine, 4.6 g. (0.35 mole) of ethyl acetoacetate, 2 g. of zinc chloride, and 10 ml. of ethanol is refluxed for 7 hours and poured into 65 ml. of water containing 1 ml. of concentrated hydrochloric acid. After standing, the solid is collected, dissolved in a small amount of concentrated hydrochloric acid and the mixture poured into about 100 ml. of water. Again, the solid is collected, and then recrystallized from ethanol twice to provide 3 g. of light tan needles melting at 151°–152°C.

Analysis Calculated for $C_{16}H_{17}NO_2$: C, 75.3; H, 6.7; N, 5.5. Found: C, 75.2; H, 6.6; N, 5.6.

EXAMPLE 5

Preparation of
Cyclopent[c]julolidino[9,10-e]11H-pyran-11-one

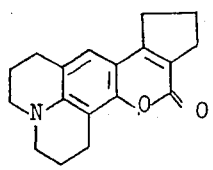

A mixture of 5.7 g. (0.03 mole) of 8-hydroxyjulolidine, 5.2 g. (0.035 mole) of the ethyl and methyl mixed esters of cyclopentanone carboxylate, sold by Aldrich Chemicals, 2 g. of zinc chloride, and 10 ml. of ethanol is refluxed overnight and poured into 65 ml. of water and 1 ml. of hydrochloric acid. After standing, the solid is collected, dissolved in concentrated hydrochloric acid and the solution poured into water, Again, the solid is collected and recrystallized from ethanol three times to yield 2 g. of product melting at 150°–151°C. mp = 150°–151°C. Yield = 2 g.

Analysis Calculated for $C_{18}H_{19}NO_2$: C, 76.8; H, 6.8; N, 5.0. Found: C, 77.1; H, 6.7; N, 4.8.

EXAMPLE 6

Preparation of
11-(2-Carboxyphenyl)dipyrrolino[3,2-b;2,3-i]xanthylium chloride

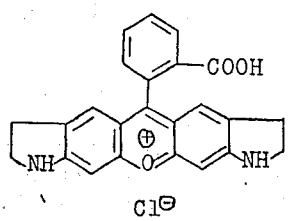

A mixture of 3 g. of phthalic anhydride, 3 g. of 6-hydroxyindoline, and 1.5 g. of zinc chloride is heated in an oil bath at 165°C for 5 hours with stirring. The melt is cooled, powdered and washed with hot water. The solid is dissolved in warm, dilute sodium hydroxide solution and filtered. The filtrate is made strongly acidic with hydrochloric acid, allowed to stand, and the solid collected, boiled with 300 ml. of ethanol and filtered hot. The filtrate is evaporated to dryness, the residue recrystallized from methanol and chromatographed as in Example 2. The infrared spectra agrees with the assigned structure for the chloride salt. The chloride salt can be converted to the perchlorate salt by dissolving in warm, dilute sodium hydroxide solution, filtering and acidifying the filtrate with perchloric acid. The solid is collected, washed with water, and extracted in a Soxhlet extractor with ethanol. The extract is concentrated, chilled, and the solid perchlorate salt collected (mp > 400°C).

Analysis Calculated for $C_{24}H_{19}N_2ClO_7$: C, 59.7; H, 4.0; N, 5.8. Found: C, 60.4; H, 3.7; N, 5.6.

EXAMPLE 7

Preparation of
8-(2-Carboxyphenyl)julolidino[10,9-b]-11H-benzo-1-pyran-11-one

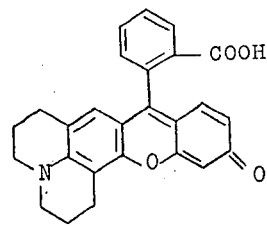

A portion of phthalic anhydride (3 g.) is heated to 150°C and 3.8 g. of 8-hydroxyjulolidine are added in portions. The temperature is raised to 180°C and 2.2 g. of resorcinol dissolved in 10 ml. of 95% sulfuric acid is added. The mixture is heated at 100°C for 3 hours, cooled and poured into ice water. The solid is collected, dissolved in warm, dilute sodium hydroxide solution and filtered. The filtrate is neutralized with excess acetic acid and the solid collected. The product is chromatographed on silica gel using 1:1 methanol:chloroform, then on neutral alumina using methanol. A sample produced a single spot upon analysis by thin layer chromatography.

EXAMPLE 8

Preparation of
13-(2-Carboxyphenyl)dipyridino-[3,2-b;2,3-i]-1,2,3,4,9,10,11,12-octahydroxanthylium perchlorate

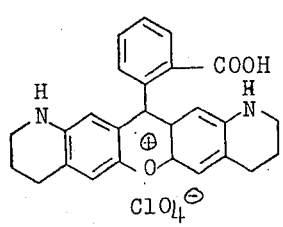

A mixture of 7 g. of 7-hydroxy-1,2,3,4-tetrahydroquinoline, 7 g. of phthalic anhydride, and 3 g. of zinc chloride is heated with stirring in an oil bath at 165°C for 5 hours and cooled. The solid is powdered, washed with hot water, dissolved in warm, dilute ammonium hydroxide and filtered. The filtrate is made strongly acid with perchloric acid. The solid is collected and extracted with ethanol in a Soxhlet extractor. The extracts are chilled and the solid collected to produce a yield of ½ g. of product (mp > 400°C).

Analysis Calculated for $C_{26}H_{23}N_2ClO_7$: C, 61.1; H, 4.5; N, 5.5. Found: C, 60.7; H, 4.4; N, 5.6.

EXAMPLE 9

Preparation of 9-(2-Ethoxycarbonylphenyl) 2,3,6,7,12,13,16,17-octahydro-1H,5H,11H,15H-diquinolizino[1,9-bc;1',9'-hi]xanthylium chloride One gram of dye prepared as described in Example 2 is dissolved in 100 ml. of ethanol, and dry hydrogen chloride gas is passed through the solution while refluxing for 12 hours. The solution is concentrated to dryness, and the residue is treated with alcoholic perchloric acid and chilled. The sticky solid is collected, dissolved in 50 ml. of boiling ethanol, and water containing a small amount of perchloric acid is added until the solution becomes cloudy; the mixture is then chilled, and the solid ethyl ester collected. A sample produced a single spot upon analysis by thin layer chromatography.

The dyes of this invention are useful as lasing media when dissolved in a non-interfering solvent (i.e., one that does not inhibit stimulated emission). This use of the present dyes is discussed further in copending K. H. Drexhage application Ser. No. 170,348, filed Aug. 9, 1971, and entitled LASER MEDIA CONTAINING RIGIDIZED DYES. Lasing media of this type can be used, for example, in an organic dye liquid laser of the type described by Sorokin et al, *IBM Journal*, Vol. 11, p. 148, (1967).

The following additional examples are included as showing the described lasing utility. The threshold energy referred to in the following examples is defined as the light energy from the excitation source which is just sufficient to initiate lasing of the rigidized dye solution. Unless otherwise stated, the excitation source is a giant pulse from a 5,300A frequency doubled, neodymium glass laser. The rigidized dye lasing medium is placed in a cuvette which is located between two dielectric mirrors which form a nearly hemispherical dye laser cavity. The light from the excitation or pumping source passes through one of the dielectric mirrors into the dye-containing cuvette and along the optical axis of the cavity. In order to determine the threshold energy, a beam splitter is used to sample the output from the excitation source. The sampled output is measured with a calibrated photodiode. The output of the dye laser is also sampled to determine the wavelength of lasing.

EXAMPLE 10

The dye of Example 2 is mixed in methanol to an optical density of about 2.0 in a 5 cm. dye cuvette which is placed between two dielectric mirrors as described above. The dye is found to lase at about 606 nm., with a threshold energy of 0.29 millijoules. Using the dye of Example 3, it is found to lase at 606 nm. with a threshold energy of 0.30 millijoules.

EXAMPLE 11

The dye of Example 5 is mixed in methanol to an optical density of about 2.0 at its absorption maximum. The solution is placed in the shell of a heat exchange tank containing cooling coils and is circulated to and from the lasing cavity at a rate sufficient to prevent localized heating. The cuvette is 15 cm in length and 15 mm in diameter. About 10 cm. beyond each end of the cuvette is a plane dielectric flat mirror. In each instance, the lasing medium is excited by a "Sorokin-type" air discharge flashlamp, the spectral output of which is smooth (free of line sources) and similar to a black body source. The energy for the flashlamp is stored by a Cornell Dubillier 1μf. fast discharge capacitor. Thresholds recorded are the minimum voltages on the capacitor required to initiate lasing. From the threshold voltage, the threshold energy (E) is determined from the formula $E=\frac{1}{2}CV^2$ where C is the capacitance of the storage capacitor and V is the voltage across the capacitor. The dye is found to lase at about 490 nm. with a threshold energy of 50 millijoules.

The term "fused dihydroindolo moiety" as used herein has reference to a structure:

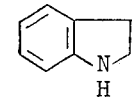

which is fused through the carbocyclic ring. A "fused(1,2,3,4) tetrahydroquinoline radical" as used herein has reference to a structure as follows:

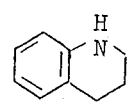

which is fused through the carbocyclic ring.

The invention has been described in detail with particular reference to certain preferred embodiments thereof, but it will be understood that variations and modifications can be effected within the spirit and scope of the invention.

I claim:
1. A compound having the formula

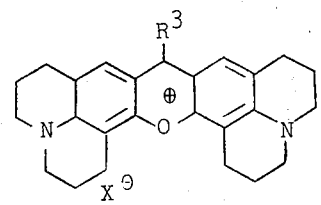

wherein
R³ represents a member selected from the group consisting of hydrogen, alkyl having 1 to 10 carbon atoms, phenyl, carboxyphenyl and ethoxycarbonyl phenyl
and X is an anion selected from the group consisting of halide, perchlorate and fluoroborate.

2. The compound as in claim 1 which is 9-(2-carboxyphenyl)-2,3,6,7,12,13,16,17-octohydro-1H,5H,11H,15H-diquinolizino[1,9-bc;1',9'-hi]xanthylium salt.

3. The compound as in claim 1 which is 2,3,6,7,12,13,16,17-octohydro-1H,5H,11H,15H-diquinolizing[1,9-bc;1',9'-hi]xanthylium salt.

4. The compound as in claim 1 which is 8-(2-ethoxycarbonyl pheny)-2,3,6,7,12,13,16,17-octohydro-1H,5H,11H,15H-diquinolizino[1,9-bc;1',9'-hi]xanthylium salt.

* * * * *

UNITED STATES PATENT AND TRADEMARK OFFICE
CERTIFICATE OF CORRECTION

PATENT NO. : 3,932,415
DATED : January 13, 1976
INVENTOR(S) : George A. Reynolds It is certified that error appears in the above-identified patent and that said Letters Patent are hereby corrected as shown below:

Col. 6, lines 56-68    The name of the compound and its structural formula should be 1,2,3,4,8,9,10,11-Octahydro-6-(2-carboxyphenyl)-dipyrido [3,2-b:2',3'-i]xanthylium perchlorate

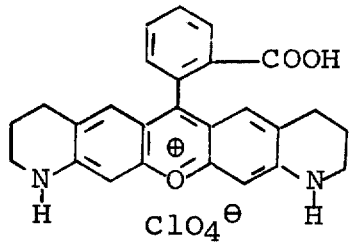

Col. 8, lines 48-57    The structural formula should be
(Claim 1)

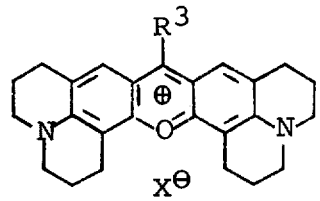

Signed and Sealed this

Second Day of November 1976

[SEAL]

Attest:

RUTH C. MASON
*Attesting Officer*

C. MARSHALL DANN
*Commissioner of Patents and Trademarks*